US010532467B2

(12) United States Patent
Diolaiti et al.

(10) Patent No.: US 10,532,467 B2
(45) Date of Patent: Jan. 14, 2020

(54) USER SELECTION OF ROBOTIC SYSTEM OPERATING MODES USING MODE DISTINGUISHING OPERATOR ACTIONS

(71) Applicant: Intuitive Surgical Operations, Inc., Sunnyvale, CA (US)

(72) Inventors: Nicola Diolaiti, Menlo Park, CA (US); Daniel H. Gomez, Los Gatos, CA (US); Probal Mitra, Sunnyvale, CA (US); Tabish Mustufa, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 353 days.

(21) Appl. No.: 15/412,657

(22) Filed: Jan. 23, 2017

(65) Prior Publication Data
US 2017/0129108 A1 May 11, 2017

Related U.S. Application Data

(63) Continuation of application No. 13/768,187, filed on Feb. 15, 2013, now Pat. No. 9,586,323.
(Continued)

(51) Int. Cl.
*G06F 19/00* (2018.01)
*B25J 13/06* (2006.01)
(Continued)

(52) U.S. Cl.
CPC ............. *B25J 13/065* (2013.01); *A61B 34/25* (2016.02); *A61B 34/30* (2016.02); *A61B 34/35* (2016.02);
(Continued)

(58) Field of Classification Search
CPC ........ B25J 13/065; B25J 13/04; B25J 9/1689; B25J 13/06; A61B 34/25; A61B 34/35;
(Continued)

(56) References Cited

U.S. PATENT DOCUMENTS 5,300,926 A    4/1994  Stoeckl
5,983,601 A *  11/1999 Blanch .................... B65B 43/60
                                                    53/118

(Continued)

FOREIGN PATENT DOCUMENTS

CN       1287522 A     3/2001
CN     101112329 A     1/2008
(Continued)

OTHER PUBLICATIONS

RNAlovesDNA, Instructions for Kinect Adventures: River Rush, Nov. 8, 2010.*
(Continued)

*Primary Examiner* — Ian Jen

(57) ABSTRACT

A robotic system has a plurality of user selectable operating modes. To select one of the operating modes, a user performs a distinguishing action which uniquely identifies a desired operating mode among the plurality of user selectable operating modes. A method implemented by a processor in the robotic system identifies the distinguishing action and places the robotic system in the user selected operating mode.

17 Claims, 9 Drawing Sheets

Related U.S. Application Data

(60) Provisional application No. 61/599,237, filed on Feb. 15, 2012.

(51) Int. Cl.
| | | |
|---|---|---|
| *A61B 90/00* | (2016.01) | |
| *A61B 34/30* | (2016.01) | |
| *A61B 34/37* | (2016.01) | |
| *A61B 34/00* | (2016.01) | |
| *B25J 9/16* | (2006.01) | |
| *A61B 34/35* | (2016.01) | |
| *B25J 13/04* | (2006.01) | |
| *A61B 17/00* | (2006.01) | |

(52) U.S. Cl.
CPC .............. *A61B 34/37* (2016.02); *A61B 34/76* (2016.02); *A61B 90/361* (2016.02); *B25J 9/1689* (2013.01); *B25J 13/04* (2013.01); *B25J 13/06* (2013.01); *A61B 2017/00207* (2013.01); *A61B 2017/00973* (2013.01); *A61B 2034/302* (2016.02)

(58) Field of Classification Search
CPC ......... A61B 34/76; A61B 34/37; A61B 34/30; A61B 90/361; A61B 2017/00973; A61B 2034/302; A61B 2017/00207
See application file for complete search history.

(56) References Cited

U.S. PATENT DOCUMENTS

| | | | | |
|---|---|---|---|---|
| 6,032,343 | A * | 3/2000 | Blanch | A61B 17/06 29/33 R |
| 6,081,981 | A * | 7/2000 | Demarest | A61B 17/06004 29/407.04 |
| 6,115,650 | A * | 9/2000 | Demarest | A61B 17/06004 700/245 |
| 6,659,939 | B2 | 12/2003 | Moll et al. | |
| 7,914,521 | B2 * | 3/2011 | Wang | B25J 9/1689 414/2 |
| 9,052,710 | B1 * | 6/2015 | Farwell | G05B 19/423 |
| 9,342,195 | B2 * | 5/2016 | Zhang | G06F 3/0416 |
| 9,586,323 | B2 | 3/2017 | Diolaiti et al. | |
| 2001/0045809 | A1 * | 11/2001 | Mukai | B25J 13/06 318/568.22 |
| 2002/0193908 | A1 | 12/2002 | Parker et al. | |
| 2006/0013469 | A1 * | 1/2006 | Wang | B25J 5/007 382/153 |
| 2006/0255544 | A1 | 11/2006 | Halliburton | |
| 2007/0283970 | A1 * | 12/2007 | Mohr | A61B 34/70 128/898 |
| 2008/0033240 | A1 | 2/2008 | Hoffman et al. | |
| 2008/0065108 | A1 | 3/2008 | Diolaiti | |
| 2008/0234866 | A1 | 9/2008 | Kishi et al. | |
| 2008/0255704 | A1 * | 10/2008 | Braut | B25J 13/02 700/264 |
| 2009/0036902 | A1 * | 2/2009 | DiMaio | A61B 34/10 606/130 |
| 2009/0037033 | A1 | 2/2009 | Phillips et al. | |
| 2009/0088774 | A1 | 4/2009 | Swarup et al. | |
| 2009/0088775 | A1 * | 4/2009 | Swarup | A61B 34/37 606/130 |
| 2009/0249257 | A1 | 10/2009 | Bove et al. | |
| 2009/0299524 | A1 | 12/2009 | Evans et al. | |
| 2009/0326552 | A1 | 12/2009 | Diolaiti | |
| 2009/0326553 | A1 | 12/2009 | Mustufa et al. | |
| 2010/0013775 | A1 | 1/2010 | Son | |
| 2010/0082039 | A1 | 4/2010 | Mohr et al. | |
| 2010/0082043 | A1 * | 4/2010 | Komuro | A61B 34/70 606/130 |
| 2010/0125366 | A1 * | 5/2010 | Huang | A63H 30/04 700/275 |
| 2010/0161129 | A1 | 6/2010 | Costa et al. | |
| 2010/0274087 | A1 | 10/2010 | Diolaiti et al. | |
| 2010/0332033 | A1 * | 12/2010 | Diolaiti | B25J 9/1689 700/259 |
| 2011/0118752 | A1 | 5/2011 | Itkowitz et al. | |
| 2011/0160910 | A1 | 6/2011 | Preisinger et al. | |
| 2011/0172858 | A1 * | 7/2011 | Gustin | B63H 21/213 701/21 |
| 2011/0184558 | A1 | 7/2011 | Jacob et al. | |
| 2011/0190937 | A1 | 8/2011 | Ortmaier | |
| 2011/0202068 | A1 | 8/2011 | Diolaiti et al. | |
| 2011/0276059 | A1 | 11/2011 | Nowlin et al. | |
| 2012/0323364 | A1 * | 12/2012 | Birkenbach | G06F 3/0338 700/257 |
| 2017/0129108 | A1 * | 5/2017 | Diolaiti | B25J 9/1689 |
| 2018/0111273 | A1 * | 4/2018 | Linnell | G06F 3/016 |

FOREIGN PATENT DOCUMENTS

| | | |
|---|---|---|
| KR | 20110059587 A | 6/2011 |
| WO | WO-2009158164 A1 | 12/2009 |
| WO | WO-2010039394 A1 | 4/2010 |
| WO | WO-2011038357 A2 | 3/2011 |
| WO | WO-2011060139 A2 | 5/2011 |
| WO | WO-2011060185 A1 | 5/2011 |

OTHER PUBLICATIONS

Extended European Search Report for Application No. EP20130749869, dated Jul. 9, 2015, 5 pages.
International Search Report and Written Opinion for Application No. PCT/US2013/026316, dated Jun. 10, 2013, 11 pages.
Kazi A., et al., "Next Generation Teach Pendants for Industrial Robots," Advances in Human-Robot Interaction, STAR 14, 2004, pp. 47-66.
Office Action dated Nov. 3, 2016 for Chinese Application No. 201380008910.8 filed Feb. 15, 2013, 5 pages.
Office Action dated Jul. 21, 2015 for Chinese Application No. 201380008910.8 filed Feb. 15, 2013, 21 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Oct. 30, 2018 for Japanese Application No. 20170224701 filed Nov. 22, 2017, 15 pages.
Extended European Search Report for Application No. EP18205540, dated Nov. 29, 2018, 7 pages.

* cited by examiner

US 10,532,467 B2

USER SELECTION OF ROBOTIC SYSTEM OPERATING MODES USING MODE DISTINGUISHING OPERATOR ACTIONS

CROSS REFERENCE TO RELATED APPLICATIONS

This application is a continuation application of U.S. Application No. 13/768,187 (filed Feb. 15, 2013), now U.S. Patent No. 9,586,323, which claims priority to U.S. Provisional Application No. 61/599,237 (filed Feb. 15, 2012), each of which is incorporated herein by reference.

FIELD OF THE INVENTION

The present invention generally relates to robotic systems and in particular to user selection of robotic system operating modes using mode distinguishing operator actions.

BACKGROUND OF THE INVENTION

A robotic system may have several user selectable operating modes. One way a user may select an operating mode is through a menu driven Graphical User Interface (GUI). Although this type of mode selection is very flexible and accommodates a large number of user selectable operating modes, it may be time consuming for the user to interact with the GUI. For example, if the user's hands are occupied at the time with manipulating input devices, it may be inconvenient to take a hand off one of the input devices and place it on another input device, such as a computer mouse or touchpad, to interact with the GUI.

Another way the user may select an operating mode among the several user selectable operating modes is by issuing a voice command that is recognizable by a voice recognition system. This approach has the advantages that it is relatively quick and the user's hands do not have to be taken off input devices being used at the time. However, the approach suffers from the additional cost of the voice recognition system and possible errors resulting from the voice recognition system incorrectly recognizing the user's spoken commands.

Yet another way the user may select an operating mode among the several user selectable operating modes is by activating a foot pedal. This has the advantage that the user will not be required to remove a hand from an input device being used at the time. However, when there are more than just a few user selectable operating modes, the number of foot pedals required to select an operating mode may become prohibitive from an implementation and usability perspective. For example, when there are four user selectable operating modes and each foot pedal is associated with only one of the user selectable operating modes, four foot pedals are required. The requirements that such foot pedals are easily reachable, but spaced apart sufficiently to avoid accidental pressing, make the approach prohibitive so that in practice only two or three pedals may be used.

OBJECTS AND SUMMARY OF THE INVENTION

Accordingly, one object of one or more aspects of the present invention is a robotic system and method implemented therein that facilitates user selection of an operating mode without the user having to remove a hand from input devices being used at the time.

Another object of one or more aspects of the present invention is a robotic system and method implemented therein that facilitates user selection of robotic system operating modes in a reliable manner.

Another object of one or more aspects of the present invention is a robotic system and method implemented therein that facilitates user selection of robotic system operating modes in a timely manner.

Another object of one or more aspects of the present invention is a robotic system and method implemented therein that facilitates user selection of robotic system operating modes in a cost effective manner.

Still another object of one or more aspects of the present invention is a robotic system and method implemented therein that does not require a one-to-one correspondence between the number of devices used for selecting an operating mode and the number of available user selectable operating modes of the robotic system.

These and additional objects are accomplished by the various aspects of the present invention, wherein briefly stated, one aspect is a robotic system which is operable in a plurality of operating modes. The robotic system comprises: one or more input devices that is used in each of the plurality of operating modes; and a processor configured to select an operating mode among the plurality of operating modes by determining that the one or more input devices has been manipulated in a manner that distinguishes the selected operating mode.

Another aspect is a method for selecting one of a plurality of operating modes of a robotic system. The method comprises: selecting an operating mode among the plurality of operating modes by determining that one or more input devices that is used in each of the plurality of operating modes has been manipulated in a manner that distinguishes the selected operating mode.

Additional objects, features and advantages of the various aspects of the present invention will become apparent from the following description of its preferred embodiment, which description should be taken in conjunction with the accompanying drawings.

DETAILED DESCRIPTION

Although a medical robotic system is described herein as an example of a robotic system, it is to be appreciated that the various aspects of the invention as claimed herein are not to be limited to such types of robotic systems.

Figure 1:
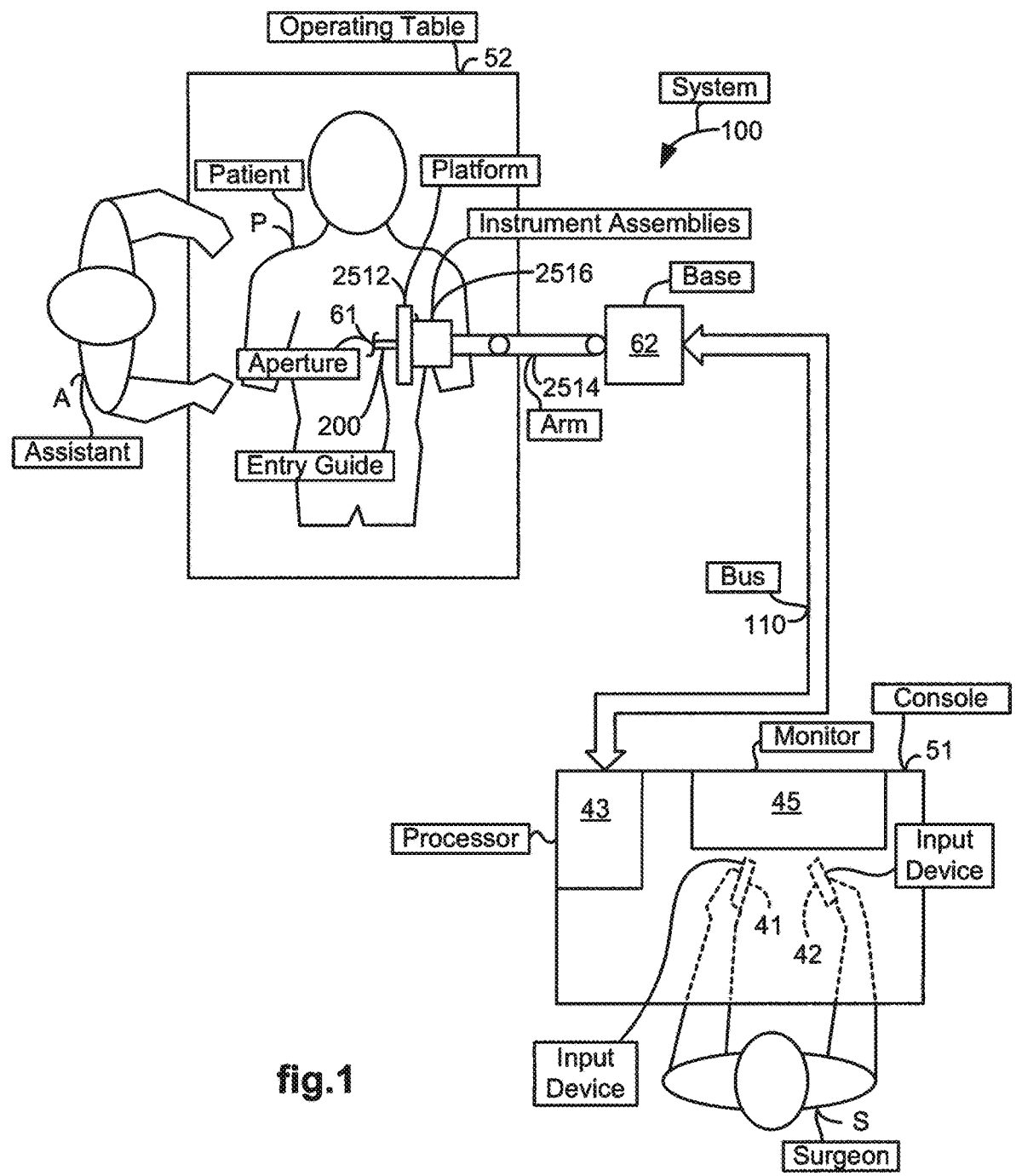
FIG. 1 illustrates a top view of an operating room employing a medical robotic system utilizing aspects of the present invention.

FIG. 1 illustrates a top view of an operating room in which a medical robotic system 100 is being employed by a Surgeon ("S") to perform a medical procedure on a Patient ("P"). The medical robotic system in this case is a Minimally Invasive Robotic Surgical (MIRS) system including a console 51 utilized by the Surgeon while performing a minimally invasive diagnostic or surgical procedure on the Patient with assistance from one or more Assistants ("A") while the Patient is on an operating table 52.

A plurality of articulated instruments is introduced to a work site within the Patient through a single entry aperture 61 by an entry guide (EG) 200. The aperture 61 may be a minimally invasive incision or a natural body orifice. The entry guide 200 is a cylindrical structure which is held and manipulated by a robotic arm assembly 2514 (also referred to herein simply as "robotic arm"). The robotic arm 2514 includes a setup arm and an entry guide manipulator. The setup arm is used to position the entry guide 200 at the aperture 61 so that a pivot point occurs at the aperture. Attached to the distal end of the robotic arm 2514 is a platform 2512 upon which instrument assemblies 2516 are mounted so that their respective instruments may extend through the entry guide 200. Each instrument assembly comprises an articulated instrument and its instrument manipulator.

Figure 2:
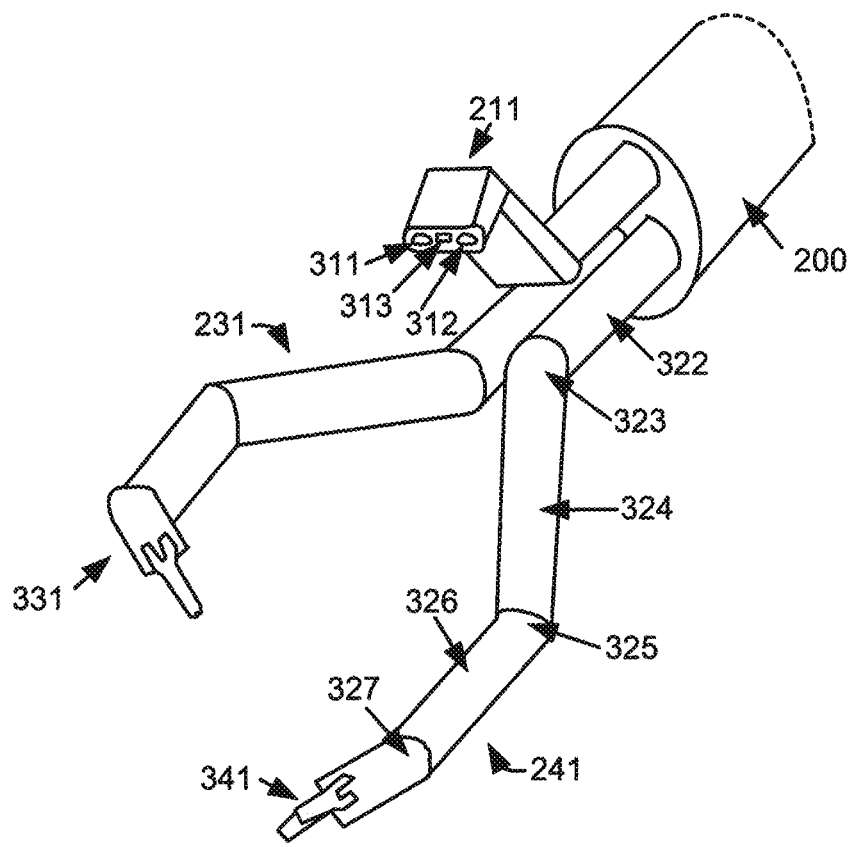
FIG. 2 illustrates a perspective view of a distal end of an entry guide with articulated instruments extending out of it in a medical robotic system utilizing aspects of the present invention.
Figure 3:
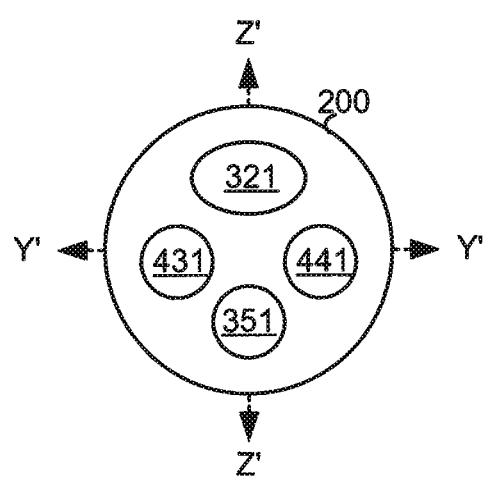
FIG. 3 illustrates a cross-sectional view of an entry guide useful in a medical robotic system utilizing aspects of the present invention.

FIG. 2 illustrates, as an example, a perspective view of the entry guide 200 with articulated instruments such as articulated surgical tool instruments 231, 241 (also referred to herein simply as "tools") and an articulated stereo camera instrument 211 (also referred to herein simply as "camera") extending out of its distal end. The camera instrument 211 has a pair of stereo image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in a cross-sectional view of the entry guide 200 in FIG. 3, a passage 351 is available for extending another articulated surgical tool through the entry guide 200 and out through its distal end. Passages 431, 441, are respectively used by the articulated surgical tool instruments 231, 241, and passage 321 is used for the articulated camera instrument 211.

Each of the articulated instruments comprises a plurality of actuatable joints and a plurality of links coupled to the joints. As an example, the second articulated instrument 241 comprises first, second, and third links 322, 324, 326, first and second joints 323, 325, and a wrist joint 327. The first joint 323 couples the first and second links 322, 324 and the second joint 325 couples the second and third links 324, 326 so that the second link 324 may pivot about the first joint 323 in pitch 292 and yaw 293 while the first and third links 322, 326 remain parallel to each other. Other tool and camera instruments, 231, 251, 211, may be similarly constructed and operated.

Figure 4:
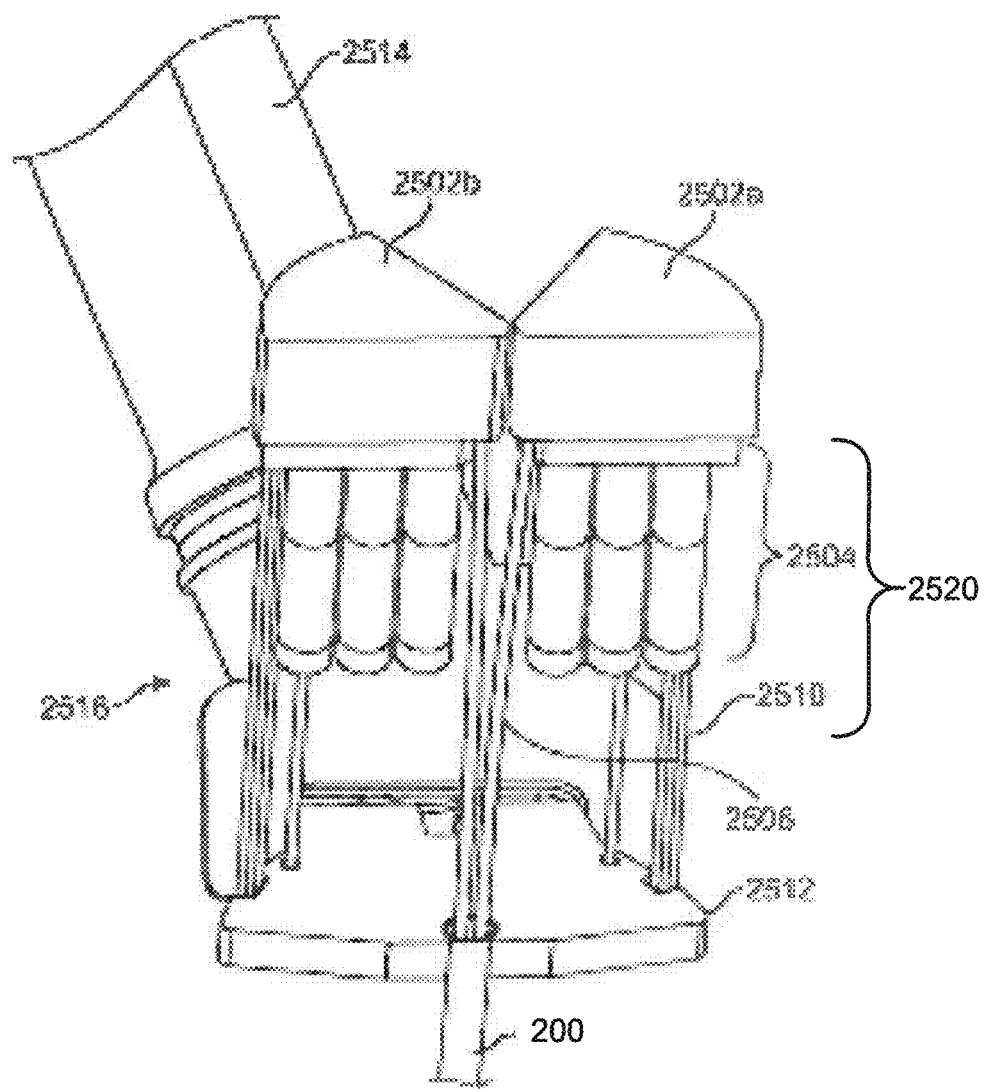
FIG. 4 illustrates a perspective view of articulated instrument assemblies mounted on a platform coupled to a robotic arm assembly in a medical robotic system utilizing aspects of the present invention.

FIG. 4 illustrates, as an example, articulated instrument assemblies 2516 mounted on the platform 2512 at a distal end of the robotic arm 2514. The entry guide 200 is attached to the platform 2512 so that entry guide 200 may be manipulated (along with the platform 2512) by the entry guide manipulator. Each articulated instrument assembly includes an articulated instrument and its instrument manipulator. For example, an exemplary articulated instrument 2502a is mounted on an actuator assembly 2504 which includes a plurality of actuators for actuating joints of the articulated instrument. Instrument 2502a has a body tube 2506 that extends past its actuator assembly 2504 and enters the entry guide 200. Actuator assembly 2504 is mounted to a linear actuator 2510 (e.g. a servocontrolled lead screw and nut or a ball screw and nut assembly) that controls the insertion and retraction of the body tube 2506 into and out of the entry guide 200. The instrument manipulator 2520 in this case comprises the actuator assembly 2504 and the linear actuator 2510. In the case where the instrument 2502a is the articulated instrument 241, the distal end of the body tube 2506 is the first link 322 shown in FIG. 2. The second instrument 2502b is mounted with similar mechanisms as shown. In addition, an articulated camera instrument may be similarly mounted.

Figure 5:
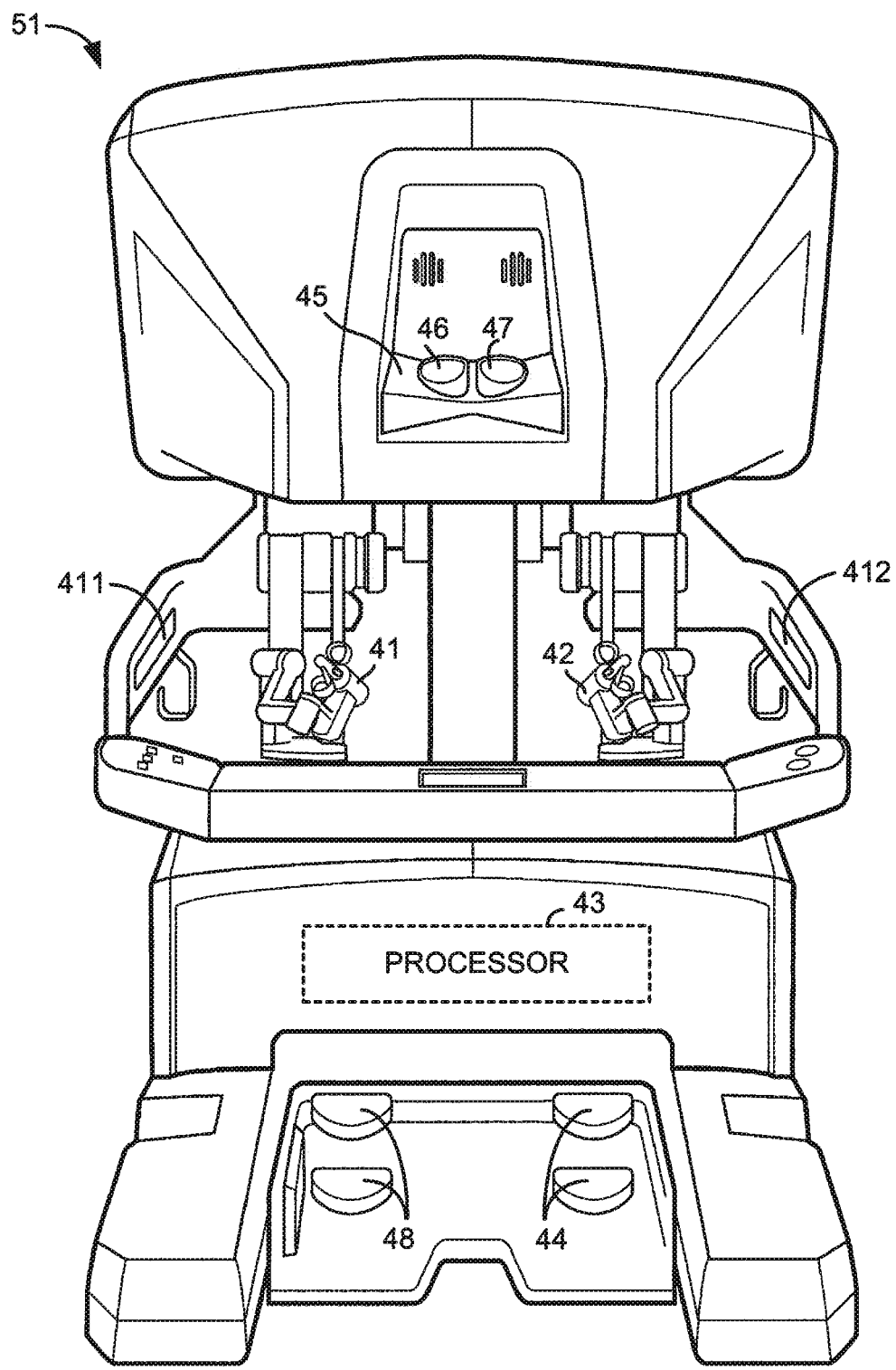
FIG. 5 illustrates a front view of a console usable in a medical robotic system utilizing aspects of the present invention.

FIG. 5 illustrates, as an example, a front view of the console 51. The console 51 has left and right input devices 41, 42 which the user may grasp respectively with his/her left and right hands to manipulate associated devices, such as the entry guide and articulated instruments, in multiple degrees-of-freedom ("DOF"). Foot pedals 44, 48 with toe and heel controls are provided on the console 51. A processor 43 is provided in the console 51 for control and other purposes as described herein. A stereo vision display 45 having left and right eyepieces, 46 and 47, is also provided for displayed stereo images that result from images captured by the stereoscopic camera instrument 211 and processed by the processor 43. The stereo view being displayed on the stereo vision display 45 may correspond to the captured image by the camera instrument 211 or it may be a digitally altered view to accommodate Surgeon preferences and/or provide telepresence to the Surgeon.

The processor 43 performs various functions in the medical robotic system. One important function that it performs is to translate and transfer the mechanical motion of input devices 41, 42 through control signals over bus 110 to command actuators in their associated manipulators to actuate their respective joints so that the Surgeon can effectively manipulate devices, such as the tool instruments 231, 241, camera instrument 211, and entry guide 200. Another function is to perform various methods and implement various controllers and cross-coupled control logic described herein.

Although described as a processor, it is to be appreciated that the processor 43 may be implemented by any combination of hardware, software and firmware. Also, its functions as described herein may be performed by one unit or divided up among different components, each of which may be implemented in turn by any combination of hardware, software and firmware. Further, although being shown as part of the console 51, the processor 43 may also comprise a number of subunits distributed throughout the system.

U.S. Publication No. U.S. 2008/0065108 A1 entitled "Minimally Invasive Surgical System," which is incorporated herein by reference, provides additional details on a medical robotic system such as the medical robotic system 100.

Robotic systems such as the medical robotic system 100 may be operated in a plurality of operating modes. Several such operating modes for the medical robotic system 100 are described in reference to FIGS. 6-8 as follows and examples of methods for selecting an operating mode among a plurality of operating modes of a robotic system are described in reference to FIGS. 9-12 as follows.

Figure 6:
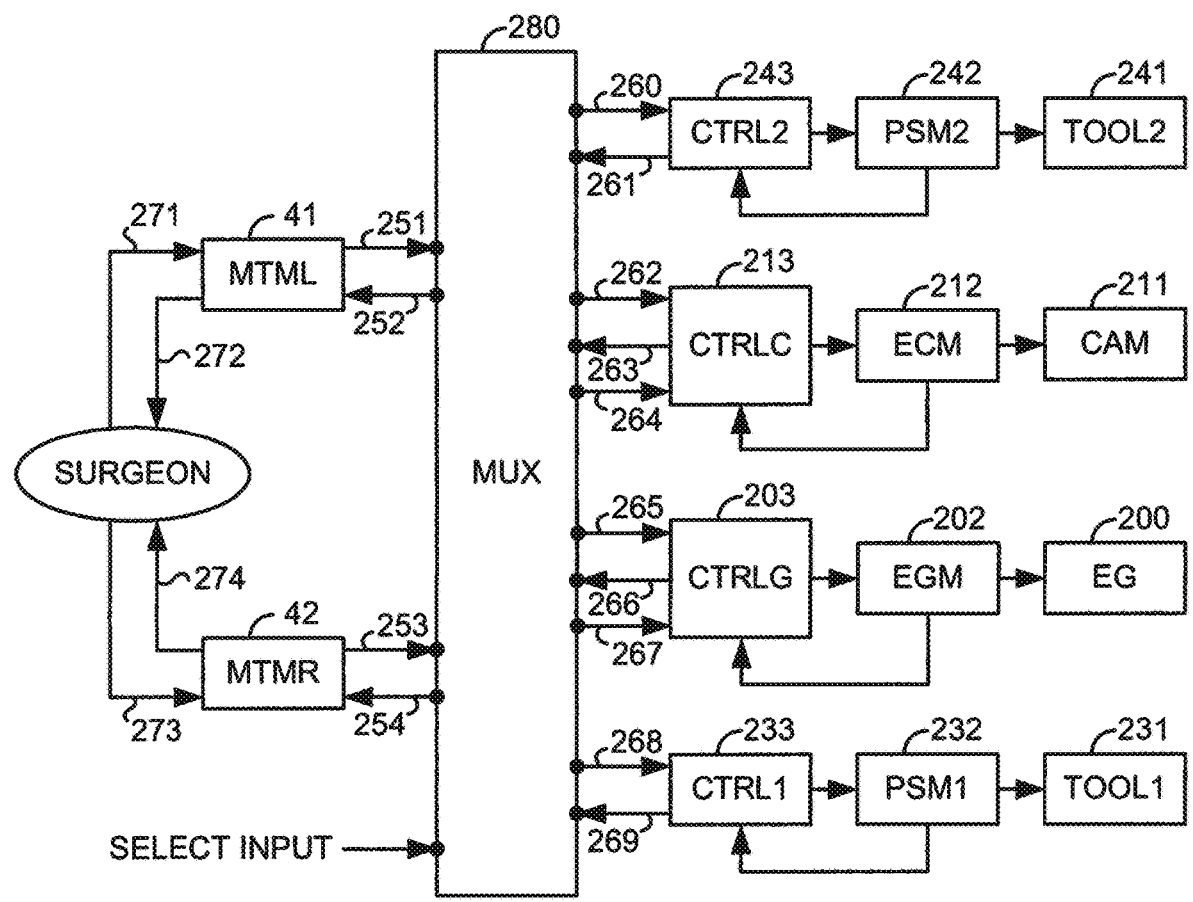
FIG. 6 illustrates a block diagram of components for controlling and selectively associating device manipulators to a pair of input devices in a medical robotic system utilizing aspects of the present invention.

FIG. 6 illustrates, as an example, a block diagram of components for controlling and selectively associating device manipulators (and their respective devices) to the input devices 41, 42 in various operating modes. Surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry aperture 61 using the setup portion of the robotic arm assembly 2514 and may be maneuvered by the entry guide manipulator (EGM) 202 of the robotic arm assembly 2514 towards the work site where the medical procedure is to be performed. Each of the devices 231, 241, 211, 200 is manipulated by its own manipulator. In particular, the camera 211 is manipulated by a camera manipulator (ECM) 212, the first surgical tool 231 is manipulated by a first instrument manipulator (PSM1) 232, the second surgical tool 241 is manipulated by a second instrument manipulator (PSM2) 242, and the entry guide 200 is manipulated by an entry guide manipulator (EGM) 202.

Each of the instrument manipulators 232, 242, 212 is a mechanical assembly that carries actuators and provides a mechanical, sterile interface to transmit motion to its respective articulated instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

Each of the input devices 41, 42 may be selectively associated with one of the devices 211, 231, 241, 200 so that the associated device may be controlled by the input device through its controller and manipulator. The operator may perform such selection using one or both foot pedals 44, 48 as described herein and other components and methods described herein. For each such selection, a select input is generated and provided to a multiplexer (MUX) 280, which is also preferably implemented by the processor 43. Depending upon the value (i.e., the combination of 1's and 0's) provided by the select input, different combinations of cross-switching are selectable.

As a first example, a first value for the select input to the MUX 280 places the left and right input devices 41, 42 in a "tool following" operating mode wherein they are respectively associated with the first and second surgical tools 241, 231. Thus, in this operating mode, the tools 231, 241 are telerobotically controlled through their respective controllers 243, 233 and manipulators 242, 232 by the Surgeon manipulating the input devices 41, 42 so as to perform a medical procedure on an anatomical structure at a work site in the Patient while the entry guide 200 is soft-locked in place by its controller 203. The camera 211 may also be soft-locked in place by its controller 213 or alternatively, it may move to automatically track movement of the end effectors 331, 341 of the tools 231, 241 so that the end effectors remain its field of view. In this configuration, the MUX 280 cross-switches to respectively connect output and input 251, 252 of the input device 41 to input and output 260, 261 of the tool controller 243; and respectively connect output and input 253, 254 of the input device 42 to input and output 268, 269 of the tool controller 233. In this way, the input devices 41, 42 may command movements of the tools 241, 231 and receive haptic feedback from their respective controllers 243, 233.

When the camera 211 or the entry guide 200 is to be repositioned by the Surgeon, one or both of the left and right input devices 41, 42 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is/are locked in place relative to the entry guide 200 by its controller.

As a second example, a second value for the select input to the MUX 280 places one of the left and right input devices 41, 42 in a single-handed, camera control mode (referred to herein simply as "camera" operating mode) wherein the input device is associated with the camera 211. Thus, in this mode, the camera instrument 211 is telerobotically controlled through its controller 213 and manipulator 212 by the Surgeon manipulating the associated input device so as to pose the camera 211 while the surgical tools 231, 241 and entry guide 200 are soft-locked in place by their respective controllers 233, 243, 203. In this configuration, assuming input device 41 is to be associated with the camera 211, the MUX 280 cross-switches to respectively connect output and input 251, 252 of the input device 41 to input and output 262, 263 of the camera controller 213. In this way, the input device 41 may command movement of the articulated camera instrument 211 and receive haptic feedback from its controller 213. The other input device 42 may be associated with another device at the time or not associated with any other device at the time. In the latter case, the input device 42 may be unused and preferably locked in place or alternatively it may be used to perform a specific function such as a computer mouse.

As a third example, a third value for the select input to the MUX 280 places the left and right input devices 41, 42 in an "two-handed, entry guide positioning mode" (referred to herein simply as "entry guide" operating mode) wherein they are associated as a pair of input devices with the entry guide 200. Thus, in this mode, the entry guide 200 is telerobotically controlled through its controller 203 and manipulator 202 by the Surgeon manipulating the input devices 41, 42 so as to pose (i.e., position and orient) the entry guide 200 while the surgical tools 231, 241 and camera 211 are soft-locked in place relative to the entry guide 200 by their respective controllers 233, 243, 213. In this case, the input devices 41, 42 may be used in tandem to control the entry guide 200, such as using a "virtual handlebar" image referenced control technique in which a point midway between pivot points of the input devices 41, 42 is used to control movement of the camera instrument 211. In this configuration, the MUX 280 cross-switches to respectively connect output and input 251, 252 of the input device 41 to input and output 265, 266 of the entry guide controller 203; and also respectively connect output and input 253, 254 of the input device 42 to input and output 265, 266 of the entry guide controller 203. The entry guide controller 203 includes logic to combine the inputs 251, 253 respectively from the input devices 41, 42 to implement the "entry guide" operational mode as described herein in reference to FIGS. 7-8 as follows.

Figure 7:
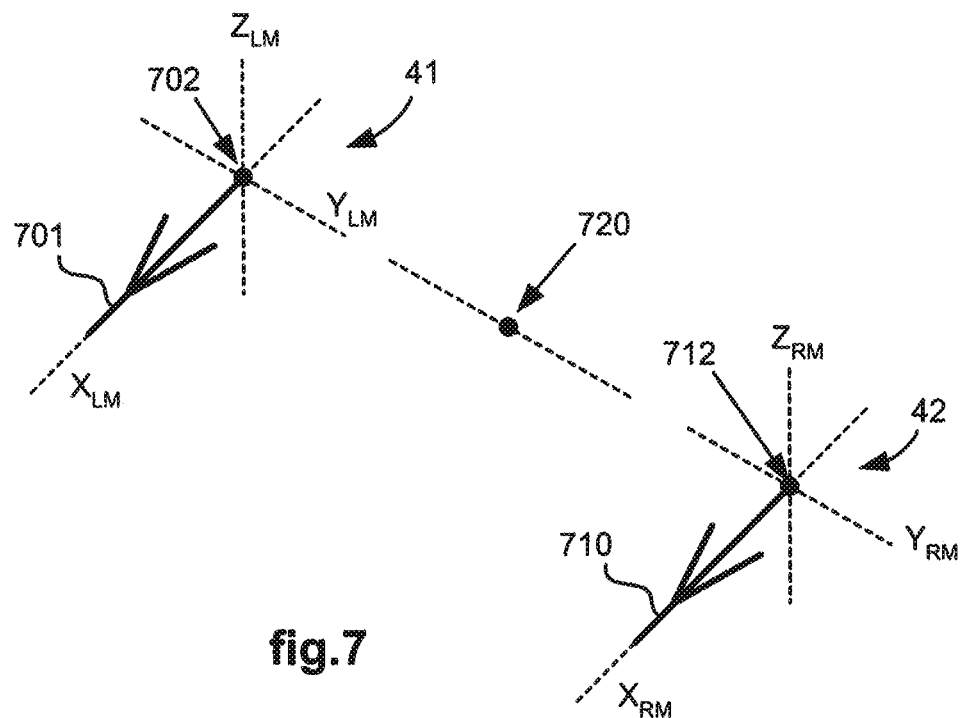
FIG. 7 illustrates reference frames for left and right input devices and a set-point defined between the input devices, as used in a medical robotic system utilizing aspects of the present invention.

FIG. 7 illustrates, as an example, movable reference frames for the input devices 41, 42. In particular, Cartesian coordinate system $X_{LM}, Y_{LM}, Z_{LM}$ having origin 702 at a tip of the left-hand input device 41 defines a first movable reference frame associated with the left-hand input device 41 and Cartesian coordinate system $X_{RM}, Y_{RM}, Z_{RM}$ having origin 712 at a tip of the right-hand input device 42 defines a second movable reference frame associated with the right-hand input device 42. Each input device in this case also has a gripper which is manually held by its user. In particular, the input device 41 has a gripper 701 and the input device 42 has a gripper 710. In a single device operation such as in "tool following" and "camera" operational modes as described above, movement of the gripper results in movement of the input device's tip reference frame relative to a fixed reference frame and results in corresponding movement of the associated device relative to a pivot point of the entry guide 200. The fixed reference frame in this case is defined so as to be at the stereo vision display 45 of the console 51 with x and y axes in the plane of the stereo image and z axis corresponding to the depth of the image.

Figure 8:
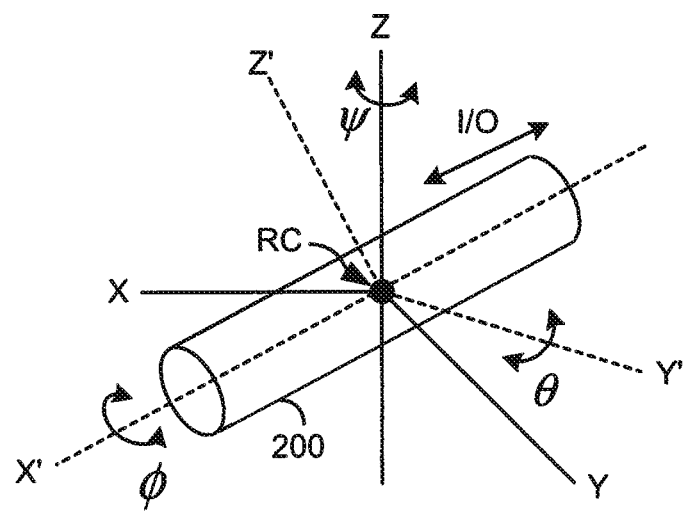
FIG. 8 illustrates a perspective view of an entry guide along with a remote center reference frame and four degrees-of-freedom movement as used in a medical robotic system utilizing aspects of the present invention.

FIG. 8 illustrates, a perspective view of a simplified (not to scale) entry guide 200. The entry guide 200 is generally cylindrical in shape and has a longitudinal axis X' running centrally along its length. The pivot point, which is also referred to as a Remote Center (RC), of the entry guide 200 serves as an origin for both a fixed reference frame having X, Y and Z axes as shown and an entry guide reference frame having X', Y' and Z' axes as shown. As previously described, the setup arm of the robotic arm 2514 holds and positions the entry guide 200 so that the Remote Center of the entry guide 200 is at the entry aperture 61 of the Patient.

When the system 100 is in the "entry guide" operational mode, the input devices 41, 42 are to be moved in a specified manner by the Surgeon to command movement of the entry guide 200. In particular, when the entry guide 200 (and the articulated instruments disposed within it at the time) is desired to be pivoted about the Z axis (which remains fixed in space) at the remote center "RC" in yaw ψ, the Surgeon moves both grippers of both input devices 41, 42 in the same direction to the right or left, depending upon which direction the entry guide 200 is be rotated (e.g., clockwise if to the left and counter-clockwise if to the right). When the entry guide 200 (and the articulated instruments disposed within it at the time) is desired to be pivoted about the Y' axis (which is orthogonal to the longitudinal axis X' of the entry guide 200) in pitch θ, the Surgeon moves the grippers of both input devices 41, 42 in the same direction up or down so that distal end of the entry guide 200 pitches down when both grippers 701, 710 are moved up and the distal end of the entry guide 200 pitches up when both grippers 701, 710 are moved down. When the entry guide 200 (and the articulated instruments disposed within it at the time) is desired to be pivoted about its longitudinal axis X' in roll Φ, the Surgeon moves the gripper of one input device upward while moving the gripper of the other input device downwards so the grippers pivot about a pivot point 720 which is mid-way between the origins 702, 712 of the movable reference frames of the input devices 41, 42. Finally, when the entry guide 200 is desired to be moved linearly along its longitudinal axis X' in insertion/retraction or in/out "I/O" directions, the Surgeon moves the grippers of both input devices 41, 42 in the same direction forward or backward so that the entry guide 200 moves forward in an insertion direction when both grippers move forward and the entry guide 200 moves backward in a retraction direction when both grippers move backward.

In addition to the three operating modes described above, a fourth value for the select input to the MUX 280 places the left and right input devices 41, 42 in a fourth operating mode (referred to herein as a "combo control" operating mode) in which the entry guide 200 is moved by the input devices 41, 42 moving in tandem as previously described in reference to the "entry guide" operating mode. However, in this mode, the end effectors 331, 341 of the instruments 231, 241 are anchored in place (i.e., maintained at the same position and orientation in a world reference frame) by their respective controllers 233, 243. In order to do this, the instrument controllers 233, 243 command their respective instrument manipulators 232, 242 to actuate their respective articulation joints (e.g., articulation joints 323, 325, 327 of instrument 241) in an appropriate manner to accommodate such anchoring of their end effectors 331, 341 in place as the entry guide 200 moves. As in the "entry guide" operating mode, the camera controller 213 commands the camera manipulator 212 to soft-lock actuatable joints of the camera 211 in place so that the image capturing end of the camera 211 may be re-oriented as the entry guide 200 is re-oriented. In this configuration, the MUX 280 cross-switches to respectively connect output and input 251, 252 of the input device 41 to the input and output 265, 266 of the entry guide controller 203; and also respectively connect output and input 253, 254 of the input device 42 to the input and output 265, 266 of the entry guide controller 203. The entry guide controller 203 includes logic to combine the inputs 251, 253 respectively from the input devices 41, 42 to implement the "entry guide" operational mode. Coupled control logic between the entry guide controller 203 and the instrument controllers 243, 233 command the instrument controllers 243, 233 to command their respective instrument manipulators 232, 242 to actuate their respective articulation joints in an appropriate manner to accommodate the anchoring of their end effectors 331, 341 in place as the entry guide 200 moves.

U.S. Publication No. 2010/0274087 A1 entitled "Medical Robotic System with Coupled Control Modes," which is incorporated herein by reference, provides additional details on coupled control modes in a medical robotic system such as the medical robotic system 100.

Figure 9:
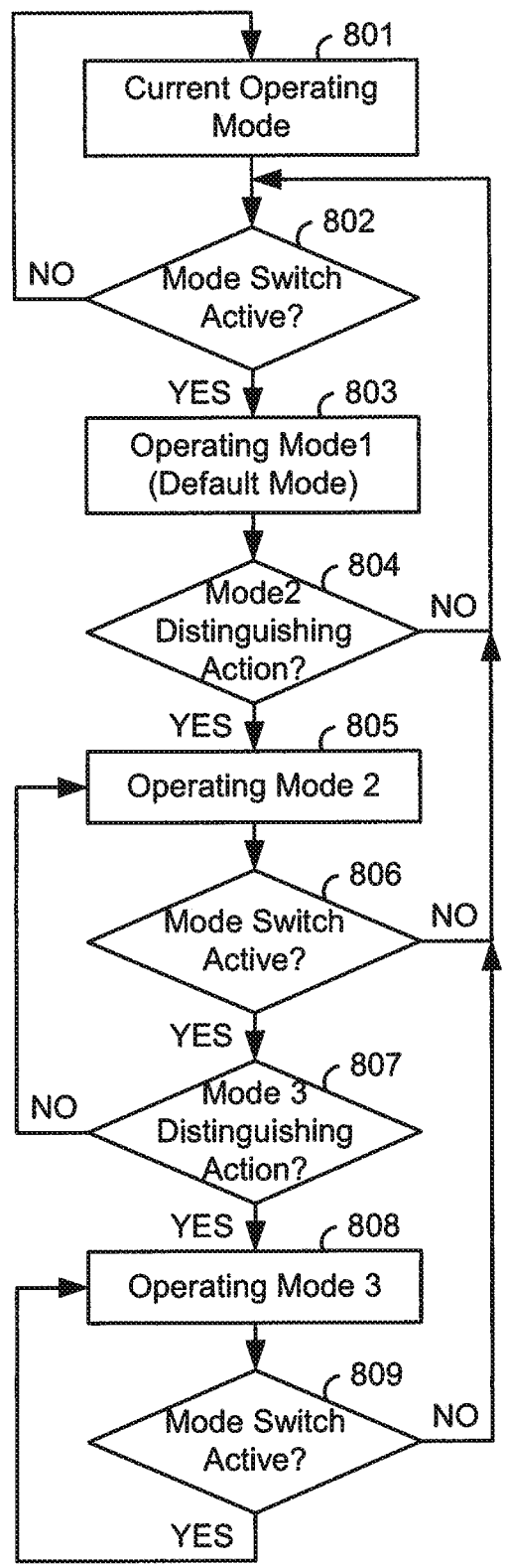
FIG. 9 illustrates a flow diagram of a method for selecting one of a plurality of operating modes of a robotic system, utilizing aspects of the present invention.

FIG. 9 illustrates a flow diagram of a method, which is implemented by a processor in a robotic system, for selecting operating modes of the robotic system. In block 801, the robotic system is in a current operating mode. As an example, the current operation mode may be a normal operating mode of the robotic system, such as the "tool following" operating mode used for performing a medical procedure on an anatomical structure of a Patient.

In block 802, the method determines whether a mode switch has been activated, such as the right foot pedal 44 of the console 51, in which case, the mode switch is activated when the Surgeon depresses it with a foot. Other examples of mode switches include depressible buttons on the input devices 41, 42, and voice commands to a voice recognition system. If the determination in block 802 is NO, then the method loops back to block 801 and keeps the robotic system in the current operating mode. On the other hand, if the determination in block 802 is YES, then in block 803, the method places the robotic system in a first operating mode (referred to herein as the default operating mode), such as the "combo control" operating mode. The default operating mode is preferably the operating mode that is most commonly selected among the user selectable operating modes available for selection at the time. By making this operating mode the default operating mode, more often than not the system will be operating in the desired operating mode without further processing delay.

In block 804, the method waits until it detects some action taken by the system user manipulating one or more input devices such as the hand-manipulatable input devices 41, 42 of the console 51. Upon detecting that an action has been taken, the method determines whether the action is a distinguishing action of a second operating mode, such as the "camera" operating mode. The term "distinguishing action" means an action that uniquely identifies the operating mode as opposed to other operating modes being considered at the time (which includes the operating mode that the robotic system is presently operating in). In particular, it is a manipulative action performed by a system user on one or both of the input devices 41, 42 that is used in the operating mode which is being selected, but not in any of the other operating modes available for selection at the time. Examples of distinguishing actions for the "camera" operating mode and the "combo control" operating mode are respectively illustrated in FIGS. 11 and 12, when these two operating modes are the only ones available for selection at the time. If the determination in block 804 is YES, then in block 805, the method places the robotic system in the second operating mode. On the other hand, if the determination in block 804 is NO, then the method returns to block 802.

While operating in the second operating mode, in block 806, the method determines whether the mode switch is still active. If the determination in block 806 is NO, then the method loops back to block 802. On the other hand, if the determination in block 806 is YES, then in block 807, the method waits until it detects some action taken by the system user manipulating one or more input devices such as the hand-manipulatable input devices 41, 42 of the console 51. Upon detecting that an action has been taken, the method determines whether the action is a distinguishing action of a third operating mode. If the determination in block 807 is YES, then the method places the robotic system in the third operating mode. On the other hand, if the determination in block 807 is NO, then the method loops back to block 805 to keep the robotic system in the second operating mode. While operating in the third operating mode, in block 809, the method determines whether the mode switch is still active. If the determination in block 809 is NO, then the method loops back to block 802. On the other hand, if the determination in block 809 is YES, then the method loops back to block 808 to keep the robotic system in the third operating mode.

Note that in the above-described method, in order to revert back to a prior operating mode, the mode switch must be released or deactivated so that the method may loop all the way back to block 802 before proceeding to the desired operating mode. For example, if the robotic system is operating at the time in the third operating mode and the system user desires to revert back to the second operating mode, the system user must first release the mode switch so the method jumps back to block 802. The system user must then reactivate the mode switch and perform an action which distinguishes the second operating mode as describe in reference to block 804.

Figure 10:
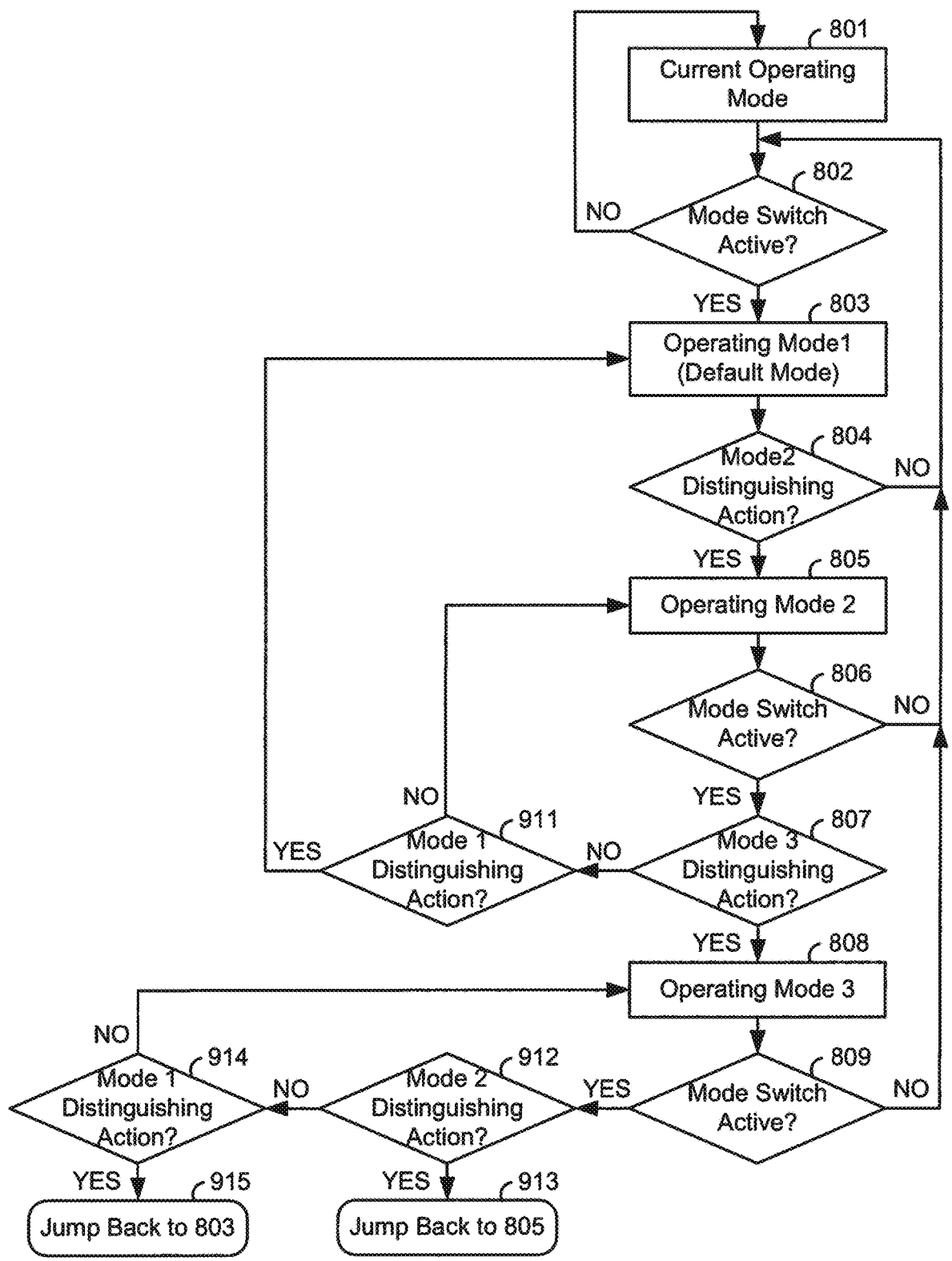
FIG. 10 illustrates a flow diagram of an alternative method for selecting one of a plurality of operating modes of a robotic system, utilizing aspects of the present invention.

FIG. 10 illustrates, as an example, a flow diagram of an alternative method, which is implemented by a processor in a robotic system, for selecting operating modes of a robotic system. This alternative method modifies the method of FIG. 9 to facilitate reversion back to a prior operating mode without having to loop all the way back to block 802. In this method, blocks 801-809 are performed in generally the same manner as described in reference to FIG. 9 with the following exceptions.

As a first exception, if the determination in block 807 is a NO, then instead of looping directly back to block 805, in block 911, the method waits until it detects some action taken by the system user manipulating one or more input devices such as the hand-manipulatable input devices 41, 42 of the console 51. Upon detecting that an action has been taken, the method determines whether the action is a distinguishing action of the first operating mode. If the determination in block 911 is YES, then the method jumps back to block 803 and places the robotic system in the first operating mode. On the other hand, if the determination in block 911 is NO, then the method loops back to block 805 to keep the robotic system in the second operating mode.

As a second exception, if the determination in block 809 is YES, then instead of looping directly back to block 808, in block 912, the method waits until it detects some action taken by the system user manipulating one or more input devices such as the hand-manipulatable input devices 41, 42 of the console 51. Upon detecting that an action has been taken, the method determines whether the action is a distinguishing action of the second operating mode. If the determination in block 912 is YES, then the method jumps back to block 805 and places the robotic system in the second operating mode. On the other hand, if the determination in block 912 is NO, then the method proceeds to block 914. In block 914, the method determines whether the action is a distinguishing action of the first operating mode. If the determination in block 914 is YES, then the method jumps back to block 803 and places the robotic system in the first operating mode. On the other hand, if the determination in block 914 is NO, then the method loops back to block 808 to keep the robotic system in the third operating mode.

As in the case of the method described in reference to FIG. 9, at any time a determination is made that the mode switch has been deactivated (i.e., the mode switch is no longer active), the method returns to block 802. As an alternative to the determinations made in blocks 802, 806, and 809, the release or deactivation of the mode switch may act as a system interrupt that automatically returns processing of the method to a processing point corresponding to block 801 in FIGS. 9 and 10.

It is noteworthy to point out that when either the "combo control" operating mode or the "camera" operating mode is the default operating mode in the above-described method, inadvertent movement of the one or more input devices by the system user will not result in unintentionally moving the end effectors 331, 341 of the tools 231, 241, since in both of these operating modes the end effectors are held in place by their respective controllers. Thus, inadvertent movement of the end effectors 331, 341 striking an object at the work site is not a concern in these two operating modes.

Up to this point in the description of various embodiments of the present invention, it has been assumed that the system user knows which user selectable operating modes are available at the time for selection and at least one distinguishing action for each of the available user selectable operating modes. In practice, however, all system users may not have this knowledge. Even experienced users may not readily recall such information while their concentrations are focused on performing a procedure using the robotic system. Therefore, the processor 43 is preferably configured to provide graphical indications of such information on the display 45 to assist system users in selecting operating modes for the robotic system in conjunction with the methods described in reference to FIGS. 9 and 10.

The methods described in reference to FIGS. 9 and 10 preferably employ conventional threshold levels and/or low pass filters in their respective determinations performed in blocks 804, 807, 911, 912, and 914 to prevent inadvertent movements of the one or more input devices by system users resulting in unintended selections of operating modes. When threshold levels are incorporated into the determinations made in these blocks, the methods preferably also provide, as a part of the actions taken in these blocks, sensory feedback to the user as the user moves the one or more input devices so as to perform the distinguishing action. In this way, the user is aware of how close to the threshold level he or she is at the time. Such sensory feedback may take the form of any one or combination of visual feedback on the stereo display 45 of the console 51, audio feedback on stereo speakers 411, 412 of the console 51, and haptic feedback on the input devices 41, 42 of the console 51. As one example, when haptic feedback on the input devices 41, 42 is provided, such feedback may increase in intensity as the manipulating of the one or more input devices 41, 42 approaches the threshold level. As another example, when audio feedback is provided on the stereo speakers 411, 412, a stereo sound may be provided that seems to come closer to the user or simply becomes louder as the manipulating of the one or more input devices 41, 42 approaches the threshold level.

Figure 11:
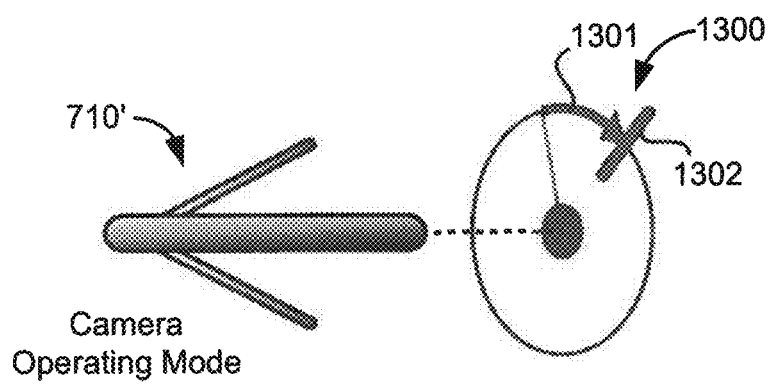
FIG. 11 illustrates a graphical indication to be displayed on a display screen for indicating a mode distinguishing action for a camera operating mode in a robotic system utilizing aspects of the present invention.
Figure 12:
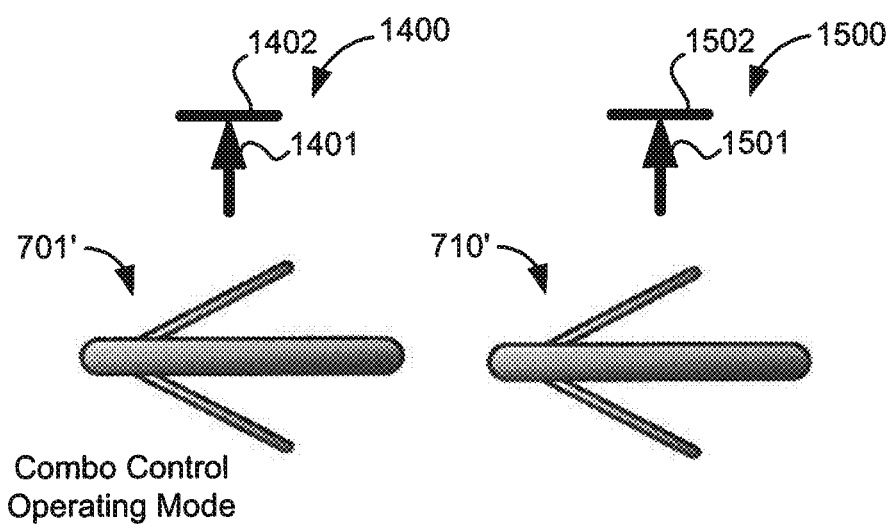
FIG. 12 illustrates a graphical indication to be displayed on a display screen for indicating a mode distinguishing action for a combo control operating mode in a robotic system utilizing aspects of the present invention.

FIGS. 11 and 12 illustrate examples of graphical information that may be provided on a display screen of a robotic system, such as the stereo vision display 45 of the medical robotic system 100, to assist the system user in selecting an operating mode in conjunction with the methods described herein. Although shown in separate figures, all operating modes that are available for user selection at the time are preferably shown together on the stereo vision display 45 so that the user knows which operating modes are user selectable at the time.

In particular, FIG. 11 illustrates a graphical representation 710' of the right gripper 710 of the right input device 42 and a graphical indication 1300 which indicates how the right gripper 710 may be moved in order to perform a distinguishing action for the "camera" operating mode when the user selectable operating modes consist of the "camera" operating mode and the "combo control" operating mode. In this example, the distinguishing action for the "camera" operating mode is a rotation of the right gripper 710 about its axis $X_{RM}$, which is an action that would not be performed in the "combo control" operating mode, thus distinguishing it from the "combo control" mode.

Although the right gripper is referenced in FIG. 11, the system user may actually perform the distinguishing action on either the left or right gripper. In one embodiment, rotation of the right gripper 710 will result in associating the right input device 42 with control of the camera movement and rotation of the left gripper 701 will result in associating the left input device 41 with control of the camera movement. In another embodiment, rotation of either the right or left gripper will result in a preselected input device being associated with control of the camera movement. Preselection in this case may be performed by system user interacting with a Graphical User Interface or any other user/system interaction means described herein or conventionally employed in robotic systems.

FIG. 12 illustrates graphical representations 701', 710' of the grippers 701, 710 of the left and right input devices 41, 42 and graphical indications 1400, 1500 which indicate how the grippers 701, 710 of the input devices 41, 42 may be moved in order to perform a distinguishing action for the "combo control" operating mode when the user selectable operating modes consist of the "camera" operating mode and the "combo control" operating mode. In this example, a distinguishing action for the "combo control" operating mode is a movement of both grippers 701, 710 in an upward direction, which is not an action that would be performed, for example, in the "camera" operating mode, thus distinguishing it from the "camera" operating mode.

The graphical indication 1300 in FIG. 11 includes a target 1302 indicative of the threshold value and an arrow 1301 indicating how close, or near, the user's manipulation of the one or more input devices is from the threshold value. Likewise, the graphical indications 1400, 1500 in FIG. 12 include targets 1402, 1502 indicative of the threshold value and arrows 1401, 1501 indicating how close the user's manipulation of the one or more input devices is from the threshold value. Although the arrows shown in the figures indicate that the threshold values have been reached, it is to be appreciated that the arrows would get progressively longer from the point in time that the movement indicating the characteristic action is first determined and the point in time that such movement reaches the threshold value as determined for their respective operating modes in blocks 804, 807, 911, 912, and 914 of FIGS. 9 and 10.

The distinguishing actions depicted in FIGS. 11 and 12 may represent either a suggested action which the system user may take to enter the indicated operating mode or it may represent the only action which the system user may take to enter the indicated operating mode. In the former case, the system is programmed to respond to any distinguishing action (with respect to all user selectable operating modes available for selection at the time) to enter the indicated operating mode. This option may be suitable for experienced system users who are knowledgeable about suitable distinguishing actions for the operating modes available for user selection at the time. In the latter case, the system is programmed to respond to only the distinguishing action shown on the stereo vision display 45 at the time to enter the indicated operating mode. This option may be suitable for inexperienced system users who lack the knowledge of which actions would be considered distinguishing actions for available operating modes and therefore may be surprised by inadvertently entering an unintended operating mode.

Note that distinguishing actions for selecting an operating mode may be different for different combinations of available operating modes. In the examples of FIGS. 11 and 12, the available operating modes are the "camera" operating mode and the "combo control" operating mode. If the available operating modes only included the "tool following" operating mode and the "camera" operating mode, however, then the indicated action for the "camera" operating mode would not distinguish it from actions that may be taken in the "tool following" operating mode. In that case, the "tool" following operating mode may be initially set as the current operating mode depicted in block 801 of FIGS. 9 and 10, and a switch to the "camera" operating mode would require a mode switch as described in reference to FIGS. 9 and 10. Alternatively, if the "camera" operating mode was selected to be the default operating mode in block 803 of FIGS. 9 and 10, a distinguishing action for the "tool following" mode would be a squeezing of either gripper 701, 710 of the input devices 41, 42, which is an action that would not be taken in either the "camera" operating mode, the "combo control" operating mode, or the "entry guide" operating mode.

Although the various aspects of the present invention have been described with respect to a preferred embodiment, it will be understood that the invention is entitled to full protection within the full scope of the appended claims.

What is claimed is:

1. A robotic system comprising:
    first and second input devices, wherein each of the first and second input devices is manipulatable both translationally and rotationally;
    first and second manipulators; and
    a processor configured to:
        cause the first and second input devices to be operatively coupled to the first manipulator, so that only concurrent translational manipulations of the first and second input devices result in a corresponding movement of the first manipulator;
        determine that the first input device has been manipulated alone in a predefined manner, wherein the predefined manner comprises a rotational manipulation of the first input device; and
        conditioned upon at least determining that the first input device has been manipulated alone in the predefined manner, cause the first and second input devices to be operatively decoupled from the first manipulator and cause at least the first input device to be operatively coupled to the second manipulator.

2. A robotic system comprising:
    first and second manipulators, wherein the first manipulator is coupled to a first device;
    first and second input devices, wherein each of the first and second input devices has a longitudinal axis, a lateral axis, and a vertical axis, and wherein each of the first and second input devices is manipulatable in: forward and backward directions along the longitudinal axis, up and down directions along the vertical axis, right and left directions along the lateral axis, rotational directions about the longitudinal axis, rotational directions about the vertical axis, and rotational directions about the lateral axis; and
    a processor configured to:
        cause the first and second input devices to be operatively coupled to the first manipulator, so that concurrent movements of the first and second input devices result in a corresponding movement of the first manipulator;
        conditioned upon the first and second input devices being operatively coupled to the first manipulator, command the first manipulator to rotate the first device in a roll rotational direction about the longitudinal axis of the first device in response to the first input device being manipulated in its up direction and the second input device being concurrently manipulated in its down direction;
        determine that the first input device has been manipulated alone in a predefined manner by determining the first input device has been rotated about its longitudinal axis without a concurrent manipulation of the second input device; and
        conditioned upon at least determining that the first input device has been manipulated alone in the predefined manner, cause the first and second input devices to be operatively decoupled from the first manipulator and cause at least the first input device to be operatively coupled to the second manipulator.

3. The robotic system of claim 2, further comprising:
    a third input device;
    wherein the processor is further configured to:
        determine that the third input device has been manipulated so as to indicate that a mode change is permitted; and
        only cause the first and second input devices to be operatively decoupled from the first manipulator and cause at least the first input device to be operatively coupled to the second manipulator after the first input device has been determined to have been manipulated alone in the predefined manner and the third input device has been determined to have been manipulated so as to indicate that the mode change is permitted.

4. The robotic system of claim 3:
    wherein the first and second input devices are hand operable devices; and
    wherein the third input device is a foot operable device.

5. The robotic system of claim 2, further comprising:
    a display;
    wherein the processor is further configured to:
        cause a graphical indication to be displayed on the display;
        wherein the graphical indication indicates to an operator of the first input device how the operator should manipulate the first input device in the predefined manner.

6. A robotic system comprising:
    first and second input devices, wherein the first input device is manipulatable in a first plurality of translational directions and a first plurality of rotational directions, the first plurality of rotational directions including a first rotational direction;
    first and second manipulators; and
    a processor configured to:
        cause the first and second input devices to be operatively coupled to the first manipulator, so that concurrent movements of the first and second input devices result in a corresponding movement of the first manipulator;

determine that the first input device has been manipulated alone in a predefined manner by determining the first input device has been manipulated beyond a threshold level in the first rotational direction without a concurrent manipulation of the second input device; and conditioned upon at least determining that the first input device has been manipulated alone in the predefined manner, cause the first and second input devices to be operatively decoupled from the first manipulator and cause at least the first input device to be operatively coupled to the second manipulator.

7. The robotic system of claim 6:
wherein the processor is further configured to:
cause sensory feedback to be provided to an operator of the first input device as the operator manipulates the first input device towards the threshold level in the first rotational direction.

8. A robotic system, which is operable in first and second operating modes, the robotic system comprising:
first and second input devices, wherein each of the first and second input devices is manipulatable both translationally and rotationally;
first and second manipulators, wherein only concurrent translational manipulations of the first and second input devices result in commanding movement of the first manipulator in the first operating mode; and
a processor configured to:
operate according to the first operating mode, in which, both the first and second input devices are concurrently used to command movement of the first manipulator;
determine that the first input device has been manipulated alone in a predefined manner, wherein the predefined manner comprises a rotational manipulation of the first input device; and
in response to at least determining that the first input device has been manipulated alone in the predefined manner, operate according to the second operating mode, in which, at least the first input device is used to command movement of the second manipulator.

9. The robotic system of claim 8:
wherein the first manipulator is coupled to a first device;
wherein each of the first and second input devices has a longitudinal axis, a lateral axis, and a vertical axis;
wherein each of the first and second input devices is manipulatable in: forward and backward directions along the longitudinal axis, up and down directions along the vertical axis, right and left directions along the lateral axis, rotational directions about the longitudinal axis, rotational directions about the vertical axis, and rotational directions about the lateral axis;
wherein the processor is further configured to:
conditioned upon the first and second input devices operating in the first operating mode, command the first manipulator to rotate the first device in a roll rotational direction about the longitudinal axis of the first device in response to the first input device being manipulated in its up direction and the second input device being concurrently manipulated in its down direction; and
determine that the first input device has been manipulated alone in the predefined manner by determining the first input device has been rotated about its longitudinal axis without a concurrent manipulation of the second input device.

10. The robotic system of claim 8, further comprising:
a third input device;
wherein the processor is further configured to:
determine that the third input device has been manipulated so as to indicate that a mode change is permitted; and
conditioned upon determining that the first input device has been manipulated alone in the predefined manner and upon determining that the third input device has been manipulated so as to indicate that the mode change is permitted, operate according to the second operating mode.

11. The robotic system of claim 10:
wherein the first and second input devices are hand operable devices; and
wherein the third input device is a foot operable device.

12. The robotic system of claim 8, further comprising:
a display;
wherein the processor is further configured to:
cause a graphical indication to be displayed on the display;
wherein the graphical indication indicates to an operator of the first input device how the operator should manipulate the first input device in the predefined manner.

13. A robotic system, which is operable in first and second operating modes, the robotic system comprising:
first and second manipulators;
first and second input devices, wherein the first input device is manipulatable in a first plurality of translational directions and a first plurality of rotational directions, the first plurality of rotational directions including a first rotational direction; and
a processor configured to:
operate according to the first operating mode, in which, both the first and second input devices are concurrently used to command movement of the first manipulator;
determine that the first input device has been manipulated alone in a predefined manner by determining the first input device has been manipulated beyond a threshold level in the first rotational direction without a concurrent manipulation of the second input device; and
in response to at least determining that the first input device has been manipulated alone in the predefined manner, operate according to the second operating mode, in which, at least the first input device is used to command movement of the second manipulator.

14. The robotic system of claim 13:
wherein the processor is further configured to:
cause sensory feedback to be provided to an operator of the first input device as the operator manipulates the first input device towards the threshold level in the first rotational direction.

15. A method for changing operating modes of a robotic system, the method comprising:
using a processor to operatively couple first and second input devices to a first manipulator, so that concurrent movements of the first and second input devices result in a corresponding movement of the first manipulator, wherein each of the first and second input devices is manipulatable both translationally and rotationally;
conditioned upon using the processor to operatively couple the first and second input devices to the first manipulator, using the processor to command movement of the first manipulator only in response to concurrent translational manipulations of the first and second input devices;

using the processor to determine that the first input device has been manipulated alone in a predefined manner by using the processor to determine that the first input device has been manipulated rotationally; and conditioned upon the processor having at least determined that the first input device has been manipulated alone in the predefined manner, using the processor to operatively decouple the first and second input devices from the first manipulator and operatively couple at least the first input device to a second manipulator.

16. The method of claim 15, further comprising:

using the processor to determine that a third input device has been manipulated so as to indicate that a mode change is permitted; and using the processor to operatively decouple the first and second input devices from the first manipulator and operatively couple at least the first input device to the second manipulator only if the processor has determined that the first input device has been manipulated alone in the predefined manner and the processor has determined that the third input device has been manipulated so as to indicate that the mode change is permitted.

17. The method of claim 15, further comprising:

using the processor to cause a graphical indication to be displayed on a display, wherein the graphical indication indicates to an operator of the first input device how the operator should manipulate the first input device in the predefined manner.

* * * * *